United States Patent
Bu et al.

(10) Patent No.: US 11,253,324 B1
(45) Date of Patent: Feb. 22, 2022

(54) DETERMINATION OF APPENDIX POSITION USING A TWO STAGE DEEP NEURAL NETWORK

(71) Applicant: Cognistic, LLC, Gibsonia, PA (US)

(72) Inventors: Tom Bu, Pittsburgh, PA (US); Sanjay Chopra, Gibsonia, PA (US); Roshan Bhave, Pittsburgh, PA (US); Ji Liu, Pittsburgh, PA (US)

(73) Assignee: Cognistic, LLC, Gibsonia, PA (US)

( * ) Notice: Subject to any disclaimer, the term of this patent is extended or adjusted under 35 U.S.C. 154(b) by 281 days.

(21) Appl. No.: 16/676,110

(22) Filed: Nov. 6, 2019

(51) Int. Cl.
*G06T 7/00* (2017.01)
*G16H 30/40* (2018.01)
*G06N 3/08* (2006.01)
*A61B 34/20* (2016.01)

(52) U.S. Cl.
CPC .............. *A61B 34/20* (2016.02); *G06N 3/08* (2013.01); *G06T 7/0012* (2013.01); *G16H 30/40* (2018.01); *A61B 2034/2065* (2016.02)

(58) Field of Classification Search
CPC .............. A61B 34/20; A61B 2034/2065; G16H 30/40; G06T 7/0012; G06N 3/08
See application file for complete search history.

(56) References Cited

U.S. PATENT DOCUMENTS

| 2017/0202624 A1* | 7/2017 | Atarot | G16H 20/40 |
| 2019/0030371 A1* | 1/2019 | Han | G16H 50/20 |
| 2019/0142519 A1* | 5/2019 | Siemionow | A61B 34/10 600/408 |
| 2021/0097258 A1* | 4/2021 | Mohan | G06T 7/11 |

OTHER PUBLICATIONS

Berger et al., "Boosted Training of Convolutional Neural Networks for Multi-Class Segmentation", arXiv: 1806.05974v2, pp. 1-8 (Year: 2018).*
Kayalibay et al., "CNN-based Segmentation of Medical Imaging Data", arXiv: 1701.0305v2, pp. 1-24 (Year: 2017).*

* cited by examiner

*Primary Examiner* — Nay A Maung
*Assistant Examiner* — Jose M Torres
(74) *Attorney, Agent, or Firm* — Ference & Associates LLC (57) ABSTRACT

One embodiment provides a method for training a machine-learning model to detect a location of a person's appendix, comprising: receiving, at the machine-learning model, a plurality of images, each image being a slice of a body taken by a CT scan; identifying, for each of the plurality of images, features of the appendix, wherein the identifying comprises analyzing a plurality of slices of each of the plurality of images and classifying each of the plurality of slices, into one of a plurality of classification groups, based upon a feature of the appendix within the slice; segmenting each of the plurality of image slices included in the one of the plurality of classification groups that classifies the slice as containing the appendix, thereby identifying probable locations of the appendix, via utilizing a probability mask for each of the probable locations.

20 Claims, 5 Drawing Sheets

DETERMINATION OF APPENDIX POSITION USING A TWO STAGE DEEP NEURAL NETWORK

BACKGROUND

Acute appendicitis is the most common cause of acute-onset abdominal pain which results in emergency abdominal surgery. If caught early enough, uncomplicated acute appendicitis can be diagnosed with high accuracy using computed tomography (CT), thereby allowing for rapid treatment of the appendicitis. However, the location of the appendix within a human may fluctuate considerably, which may make it difficult to correctly setup the patient for the CT scan or to find the appendix on the images resulting from the CT scan(s). Previous studies have concluded that there are six common positions an appendix may be located within a human. Along with determining the position of the appendix, the visualization rate of the appendix in a CT examination is important. A CT examination may provide a professional with an image of a human's appendix, and depending on the appearance of appendix in the CT image, a professional can determine if the appendix comprises acute appendicitis or if the appendix is normal and may exclude a diagnosis of acute appendicitis.

BRIEF SUMMARY

In summary, one aspect provides a method for training a machine-learning model to detect a location of a person's appendix, comprising: receiving, at the machine-learning model, a plurality of images, each image being a slice of a body taken by a CT scan; identifying, for each of the plurality of images, features of the appendix, wherein the identifying comprises analyzing a plurality of slices of each of the plurality of images and classifying each of the plurality of slices, into one of a plurality of classification groups, based upon a feature of the appendix within the slice; segmenting each of the plurality of image slices included in the one of the plurality of classification groups that classifies the slice as containing the appendix, thereby identifying probable locations of the appendix, via utilizing a probability mask for each of the probable locations.

Another aspect provides an information handling device for training a machine-learning model to detect a location of a person's appendix, comprising: a processor; a memory device that stores instructions executable by the processor to: receive, at the machine learning model, a plurality of images, each image being a slice of a body taken by a CT scan; identify, for each of the plurality of images, features of the appendix, wherein to identify comprises analyzing a plurality of slices of each of the plurality of images and classifying each of the plurality of slices based upon a feature of the appendix within the slice; segment each of the plurality of image slices included in slices with the high likelihood of containing the appendix, thereby identifying probable locations of the appendix, via utilizing a probability mask for each of the probable locations; produce a binary mask, from the probability masks, encompassing at least a portion of the probable locations; and produce a smallest bounding shape within the binary mask identifying a final prediction of the location of the appendix.

A further aspect provides a product for training a machine-learning model to detect a location of a person's appendix, comprising: a storage device having code stored within, the code being executable by a processor and comprising: code that receives, at the machine-learning model, a plurality of images, each image being a slice of a body taken by a CT scan; code that identifies, for each of the plurality of images, features of the appendix, wherein the identifying comprises analyzing a plurality of slices of each of the plurality of images and classifying each of the plurality of slices based upon a feature of the appendix within the slice; code that segments each of the plurality of image slices included in the one of the plurality of classification groups that classifies the slice as containing the appendix, thereby identifying probable locations of the appendix, via utilizing a probability mask for each of the probable locations; code that produces a binary mask, from the probability masks, encompassing at least a portion of the probable locations; and code that produces a smallest bounding shape within the binary mask identifying a final prediction of the location of the appendix.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Discovery of a person having acute appendicitis will result in emergency abdominal surgery. Failure to remove a failing appendix may cause the appendix to burst and possibly cause damage to other internal parts of a human. There is only a small time window between when acute appendicitis is first recognized to when the appendix may burst, so professionals must move quickly to make sure that the appendix does not burst while still within a human. One of the symptoms of acute appendicitis is severe abdominal pain. Since severe abdominal pain can be attributed to many different diagnoses, the health professional must make sure that it is the appendix that is causing the pain to prevent unnecessary emergency surgery. Thus, to make a diagnosis of acute appendicitis, the health professional must determine the status of the appendix.

Uncomplicated acute appendicitis can be diagnosed with high accuracy with the use of computed tomography (CT). CT produces clear images of the internal organs and other tissues of a human by using multiple x-rays to produce cross-sectional images of a scanned object, for example, a human. Thus, CT images may permit a professional to diagnose a human with acute appendicitis or exclude a diagnosis prior to performing surgery.

When locating an appendix in a CT image, a professional must manually scan an image (e.g., scrolling, zooming in and out, etc.) to locate the position of an appendix. This localizing of the appendix may be time consuming because, unlike most organs, the appendix has historically been found in a variety of locations. To be more specific, analysis of past experiments and surgeries has provided professionals with the general consensus that an appendix may be found in one of six common regions with some regions being more popular than others. For example, of the six possible locations the retrocaecal region contains the appendix around 65.3% of the time, the pelvic region 31.0% of the time, the subcaecal region 2.3% of the time, the pre-ileal region 1.0% of the time, the postileal region 0.4% of the time, and the ectopic region 0.05% of the time.

Image recognition techniques have been implemented over the years to locate an appendix within the user. However, these typically require a user to manually identify features of an appendix. As mentioned previously, it is common for a professional to manually scan an image to locate the position of an appendix. However, with advances in technology, tremendous progress has been made in the field of image recognition. This can be credited to the availability of large-scale annotated datasets, the growing computational capacity of modern graphic processing units (GPU), and the revival of deep convolutional neural networks (CNN). Additionally, advances in segmentation models for professional use have taken place and have produced some outstanding products. For example, the use of fully convolutional networks (FCN) and U-Net architecture comprise a form of an encoder-decoder network. These forms of networks may force a model to capture higher level features and use them to classify pixels.

Accordingly, a system and method presented may utilize modern image recognition and modern segmentation techniques to create a neural network or machine-learning model that is able to identify the location of an appendix within an image. The system can classify slices of an image into groups indicating whether the image includes a portion of the appendix or not. A model may then segment the slices with a high-likelihood of containing an appendix, and may produce a bounding shape overlaid on an image of the predicted region containing an appendix. Thus, the system can make finding the location of the appendix in a person automated and quicker. The use of deep convolutional neural networks (CNN) for image recognition and identification of high-likelihood positions of an appendix, and then the implementation of an encoder-decoder network, for example a U-Net architecture, to segment, process, and determine which slice of an image (provided by the CNN) comprises the appendix will produce accurate predictions regarding the location of the appendix in a human. This combination of modern techniques may assist in overcoming the lengthy process professionals currently must complete when attempting to locate an appendix. Since time is of the essence when determining whether a person is suffering from appendicitis, the ability of the described system and method to decrease the time necessary for locating a patient's appendix may lead to more successful removals of an appendix before it erupts and causes further damage.

The illustrated example embodiments will be best understood by reference to the figures. The following description is intended only by way of example, and simply illustrates certain example embodiments.

Figure 1:
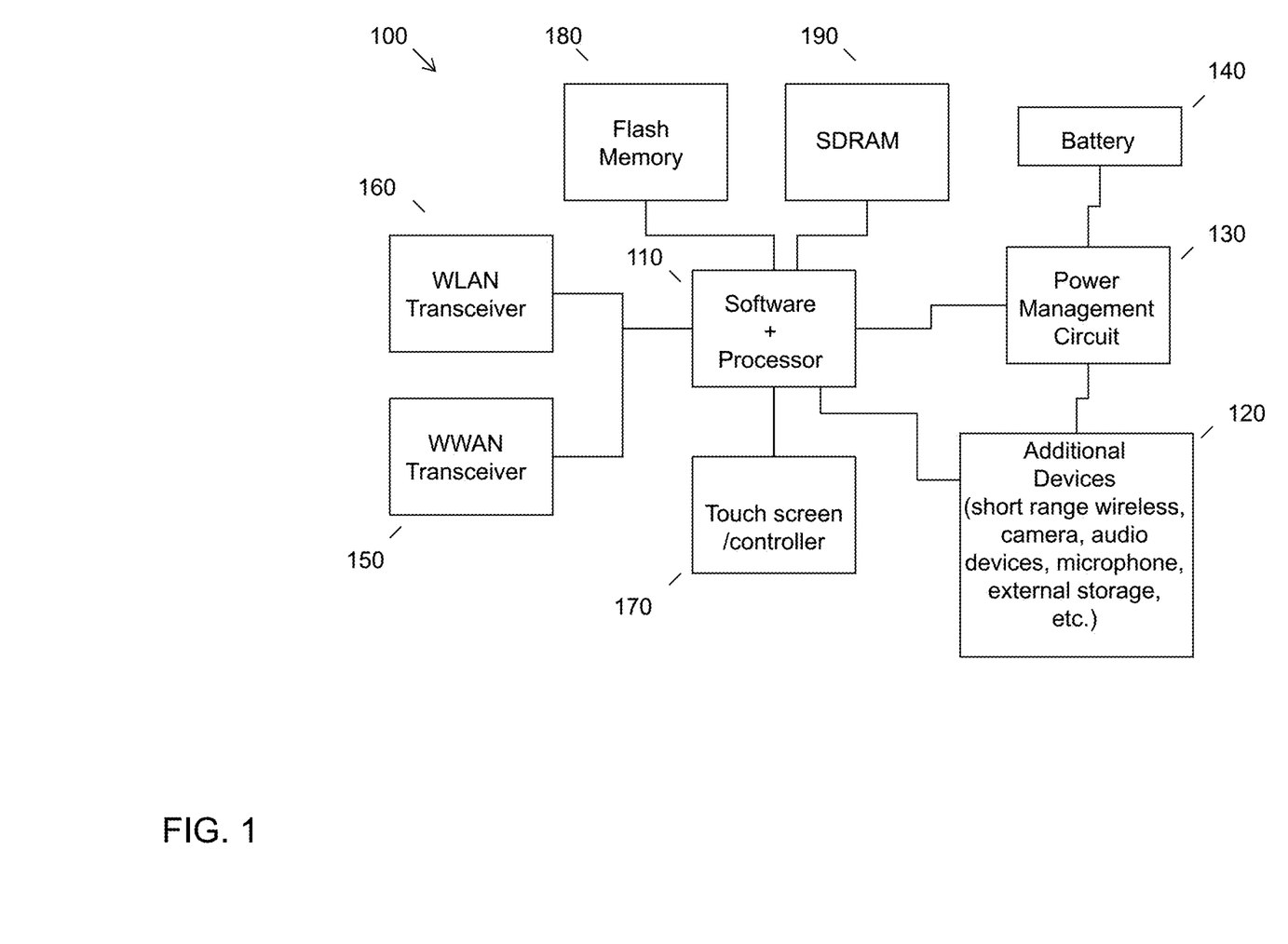
FIG. 1 illustrates an example of information handling device circuitry.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., a wireless communication device, external storage, etc. System 100 often includes a touch screen 170 for data input and display/rendering. System 100 also typically includes various memory devices, for example flash memory 180 and SDRAM 190.

Figure 2:
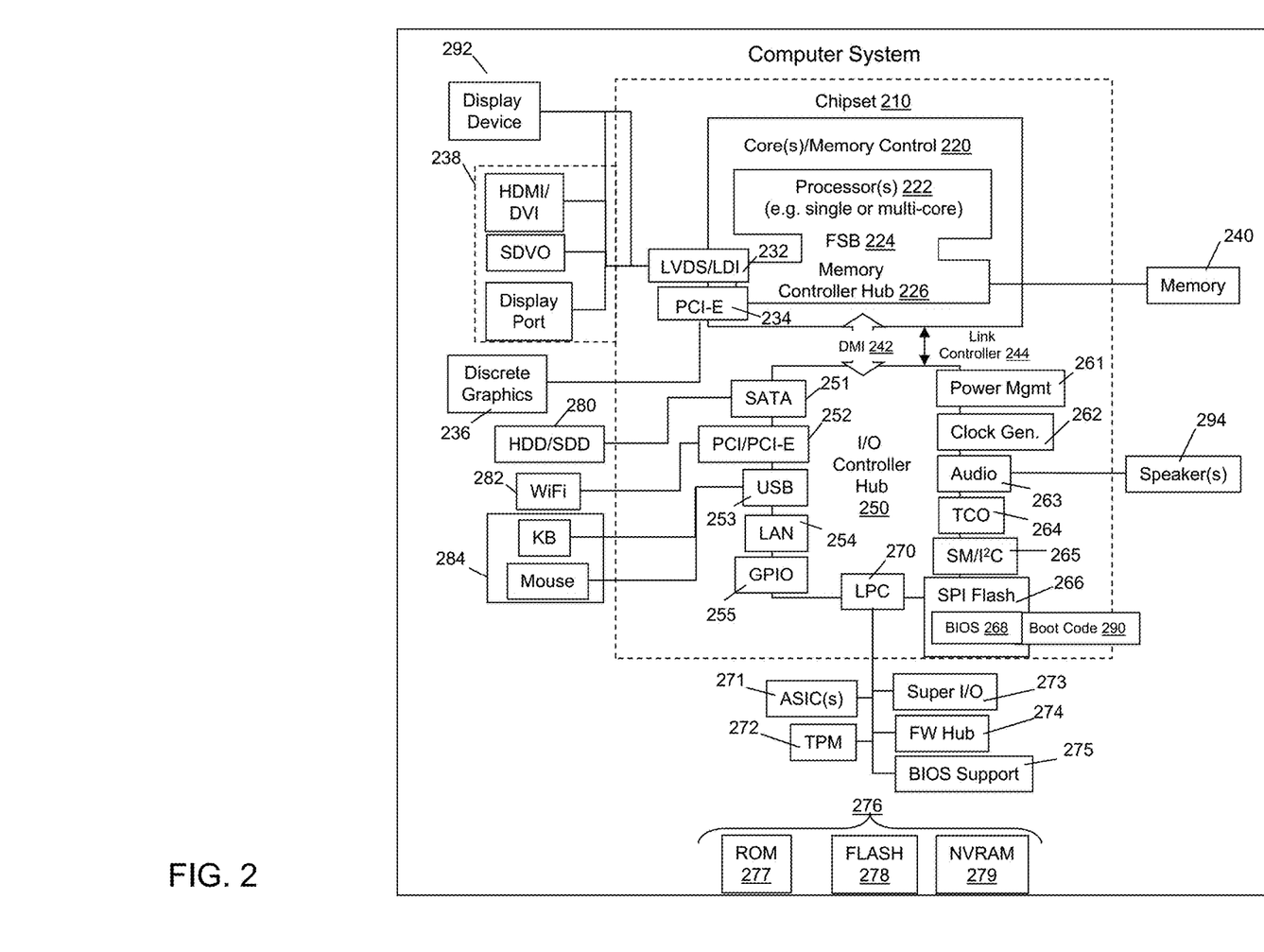
FIG. 2 illustrates another example of information handling device circuitry.

FIG. 2 depicts a block diagram of another example of information handling device circuits, circuitry or components. The example depicted in FIG. 2 may correspond to computing systems such as the THINKPAD series of personal computers sold by Lenovo (US) Inc. of Morrisville, N.C., or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as tablets, smart phones, personal computer devices generally, and/or electronic devices, which may be used to assist in determining the location of a patient's appendix. For example, the circuitry outlined in FIG. 1 may be implemented in a tablet or smart phone embodiment, whereas the circuitry outlined in FIG. 2 may be implemented in a personal computer embodiment.

Figure 3:
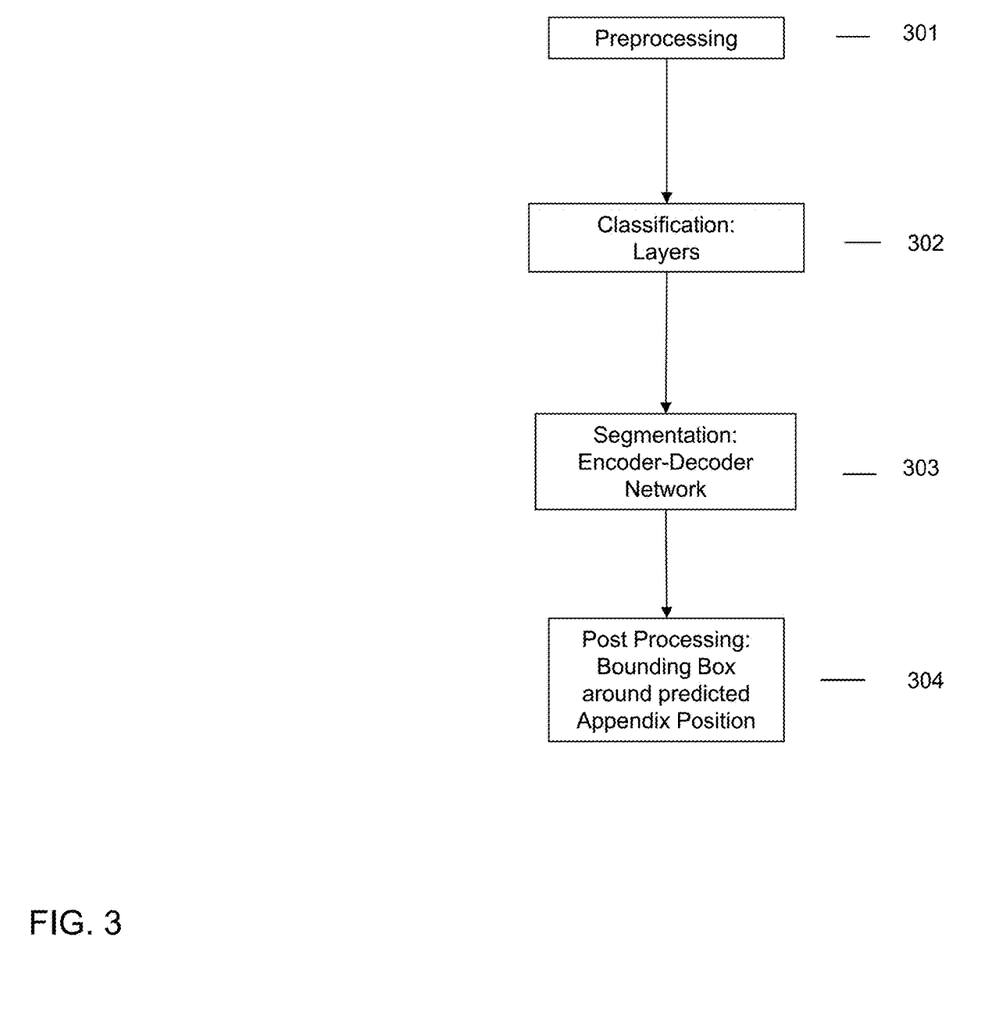
FIG. 3 illustrates an example method for appendix detection using a two stage deep neural network.

Referring to FIG. 3, the system may need to be trained prior to use so that the system can learn different features of the appendix so that it can recognize locations of appendices in patients. Thus, the first step may be training the machine-learning model, neural network, or system. The first step in this training, and subsequent appendix location identification in patients, is a preprocessing step at 301. The preprocessing may include performing image filtering, image size reduction, and the like. For example, the preprocessing may include cropping the images and removing pixels of the image not containing the appendix, removing irrelevant pixels (i.e., those pixels not including the appendix) from the images, and the like.

Accordingly, in an embodiment, the training data may be composed of a plurality of cropped digital imaging and communication in medicine (DICOM) images to produce images that are tightly cropped around a human's torso. The cropped images may also cut out CT table information that is usually present on a DICOM image. For ease of readability, the term CT image will be used here throughout to refer to the preprocessed images. By cropping a DICOM image to turn it into a CT image, an image is able to vastly reduce the number of irrelevant pixels, by about 60%, and a CT image may be resized to comprise a 512×512 pixel image. In an embodiment, the pixels of the now 512×512 pixel image may be normalized and rescaled to [0, 1] to assist in smoother calculations used later on. An embodiment may also utilize a soft-tissue window of [−160, 240] Hounsfield Units, which is often used to provide clarity of an image to a professional, or anyone else who may be viewing the image, in order to provide the same clarity to the system.

A plurality of updated CT images including images of appendices in different locations may be fed into a system and processed to provide a system with the information necessary to determine the position of an appendix. In the training phase, the location of the appendix in each of the images is already known. In an implementation phase or deployed phase, the location of the appendix is not known. For example, the implementation or deployed phase may be when the system is deployed to assist in locating the appendix of a patient. In both the training and deployment stage, the system performs all the described steps. The difference between the two stages is whether the appendix location is known or not. The more images that the system receives, the more the system is able to learn and refine its ability to accurately locate appendices in patients. A variety of images having the appendix in different locations is important for the training of a system because it introduces a system to the multiple locations that an appendix may be located, thereby allowing the system to learn different appendix features in order to accurately identify locations of appendices.

Figure 4:
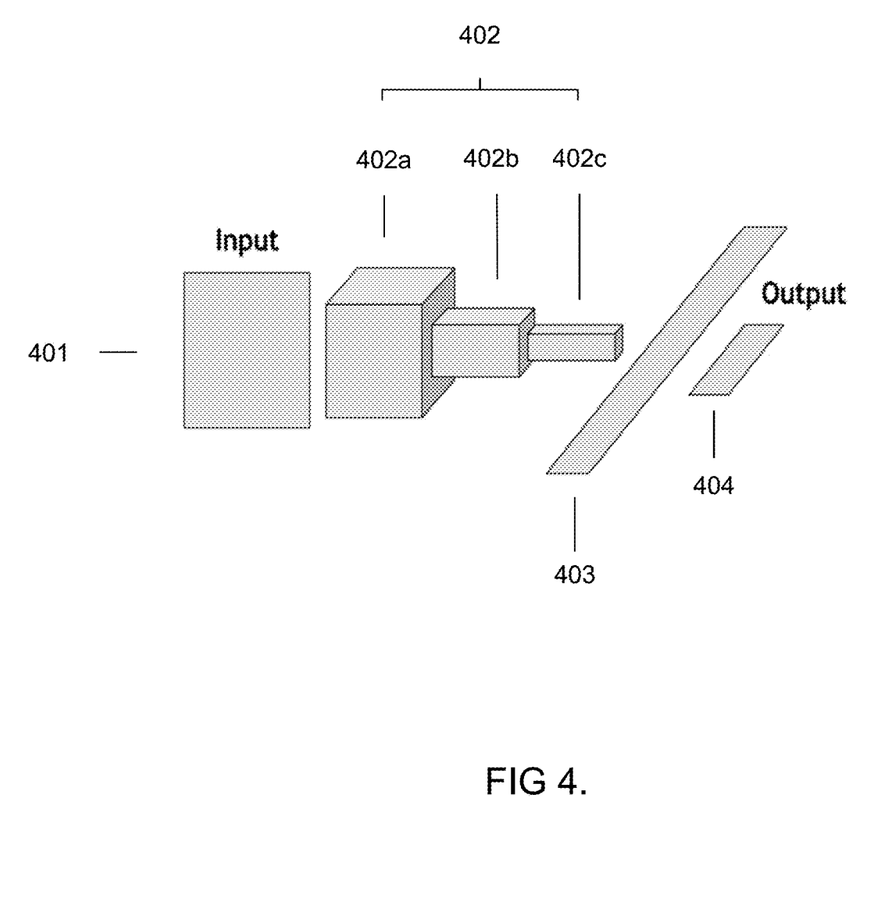
FIG. 4 illustrates an example method for the first stage of the two stage deep neural network.

Referring to FIG. 3 at 302, and FIG. 4 at 401, in an embodiment, the system may identify features of the appendix by classifying different portions of the images. The system may divide or slice each of the images into smaller portions. The system may then use a convolutional neural network (CNN) to discriminate between slices of an image that may comprise the appendix. In other words, the neural network or machine-learning model may classify each of the slices into groups including a group of image slices that include a portion of the appendix and a group of image slices that do not include a portion of the image.

In an embodiment, the neural network may include three cascaded layers containing convolutional filters 402. Between each convolutional layer, a system may provide a max-pooling operation. A max-pooling operation may recognize features affiliated with an appendix, and may summarize feature responses associated with an appendix in each pixel of an image. In an embodiment, the first of the three layers of convolutional filters 402a may provide a system with the ability to obtain the proposed regions that an appendix may be located. Potential locations of an appendix may be recognized based on features present in each slice of a CT image. After the preprocessing of an image, a system may concentrate on locating notable appendix features present in a new CT image. This recognition of features in each slice may assist in allowing a system to accurately predict potential locations of the appendix on a new CT image.

In an embodiment, each slice of an image that is being processed in a system may be classified and grouped with similar slices of an image based on features within the slice. Not all of the CT image slices will include appendix specific features. For example, other body parts and blank areas may be the only features present in a slice of the image. The slices of the image that contain appendix features may first be grouped together based simply on the presence of an appendix feature. In an embodiment, the plurality of classification groups may be compared with information related to past CT images to assist in accurately determining and classifying a feature.

After the information passes through the first cascaded layer of convolutional filters 402a, it is further processed using max-pooling to summarize found features related to the location of the appendix. In an embodiment, the summarization using max-pooling may condense the found features after passing through the first layer. Max-pooling may permit a system to use the maximum value associated with the values present in a square window, and because of the use of a single value from a plurality of values, a system may learn and implement information related to the features more quickly. Additionally, the use of the maximum value present aside from the other values may allow a system to accurately make assumptions regarding the other features present in a window. The decrease in size and reduction of dimensionality by using a single, maximum value present in a window may allow information to travel more smoothly through a system, as well. For example, a 2×2 window may comprise four total pixels within it, but after max-pooling the window a single maximum value retrieved from the four values associated with the four pixels, respectively, may be utilized to accurately describe the entire window. As mentioned previously, assumptions can be made by a system stemming from the information provided by the maximum value.

In an embodiment, in summarizing the features present in each slice of a CT image, a system may be restricted to provide a feature summarization relative to the pixels in the CT image. Restricting summarizations with respect to each pixel may allow a system to provide responses without overlapping information between neighboring pixels. Neighboring pixels may include a portion of an appendix feature, and conventionally the entire pixel including a portion of a feature will be accounted for. However, accounting for the entire pixel will result in a repetition of feature response information, which may influence and cause inaccuracies in future parts of the process. In an embodiment, the pixel specific feature responses will permit a system to relay the feature responses to the next layer in a concise manner.

The second cascaded layer of convolutional filters 402b may reject the majority of pixels left on an image that do not pertain the appendix. An embodiment may reject unnecessary or irrelevant pixels in an attempt to assist with the clarity of the image, and more importantly assist in providing a clear view of the appendix. The second layer 402b is primarily directed to the slices of the CT image that include appendix features, or the summarized feature responses provided after the first layer 402a. In an embodiment, the convolutional filters may further process an image to determine if the appendix features provided by the first convolutional layer 402a are accurate. A second layer 402b may confirm the features are present, or may determine that a feature is interpreted incorrectly by the first layer 402a. The second layer 402b may further recognize any features that may have been missed by the first convolutional filter 402a. For example, appendix features may be overlooked by the first layer 402a due to the size of the image being processed by the first convolutional filter 402a. Thus, since the second convolutional filter 402b was able to decrease the size of the image by removing blank pixels or other pixels not including an appendix feature, the second convolutional filter 402b may be able to identify features related to the appendix that initially could not be seen.

Similar to the summarization that occurs after an image passes through the first cascaded layer comprising convolutional filters 402a, the system may perform a max-pooling operation to summarize found features related to the location of the appendix after passing through the second convolutional filter 402b. At this point, since the CT image has gone through two filter layers, the number of slices containing an appendix feature may be less than the number of slices identified as containing appendix features after going through the first cascaded layer 402a only. As mentioned previously, when summarizing the appendix feature responses each summarization may be restricted to a pixel to assure that neighboring pixel information does not get accounted for.

As the summarized feature responses are fed into the third cascaded layer including convolutional filters 402c, a system may break down CT image slices more to affirm the appendix features recognized after the second layer 402b are accurate. Regressions regarding the appendix features continue through this layer in an attempt to narrow down the amount of features responses to be used to predict the location of an appendix. The feature responses may then, once again, be summarized using max-pooling. In an embodiment, this may be the last max-pooling operation used during the first stage of the model to summarize the present appendix features and the slices in which they are located. The amount of appendix feature response summaries, at this point, should be lesser than may be found after the first 402a and second layer 402b summarizations.

After the appendix feature responses have passed through the three cascaded layers of convolutional filters 402, the feature responses may be fed into two fully-connected neural layers 403. These two fully-connected layers 403 may learn how to interpret the feature responses to make appendix specific classifications. Based on the feature responses provided by the three layers 402, the two fully-connected neural layers 403 may utilize the already classified features including slices of the appendix that contain a similar classification feature to further provide appendix-specific classifications. After the appendix-specific classifications have been, and the features are fed into a final softmax layer 404.

A softmax layer 404 may be utilized to provide a probability regarding the position of an appendix. In an embodiment, to assist in producing accurate probabilities for the position of the appendix, a system may use a DropOut method. A DropOut method may be implemented during training of the convolutional neural network to assist in restricting overfitting data, for example, assisting that neighboring pixel data is not interpreted when concentrating on a single pixel, as mentioned previously. The DropOut method may ensure that, as the classification data is being interpreted, the data remains affiliated with a classification group and avoids overfitting. Overfitting would occur if data associated with a neighboring pixel is classified with a pixel being concentrated on. Additionally, a DropOut method may prevent the use of a standard parameters to assist with generalization. In an embodiment, a DropOut may behave as a regularizer when training the CNN, which may prevent the co-adaptation of units in a system. The ability to work independently and without standard parameters may permit a system to accept a wider variety of information that may not fit into conventional uses of a DropOut method. Increasing the amount of information that may be allowed into a system may assist in gaining valuable new data, as well as may permit generalizations.

In addition to the use of a DropOut method to ensure that information regarding the probability of a position of an appendix is accurate, an embodiment may utilize rectified linear units (ReLU) as a neuron activation function to assist a system in maintaining a high-speed process. The use of batch normalization may also assist in maintaining this high-speed system. ReLU may assist a system in translating the information produced, regarding the probability of the location of the appendix, to an understandable output signal. ReLU may permit a system to function at its greatest potential, and may also provide information to the segmentation aspect of the process. Regarding batch normalization, the activations affiliated with using ReLU may be adjusted and scaled so that the information provided by the three cascaded layers of convolutional filters and two fully-connected neural layers may be understood and utilized.

Figure 5:
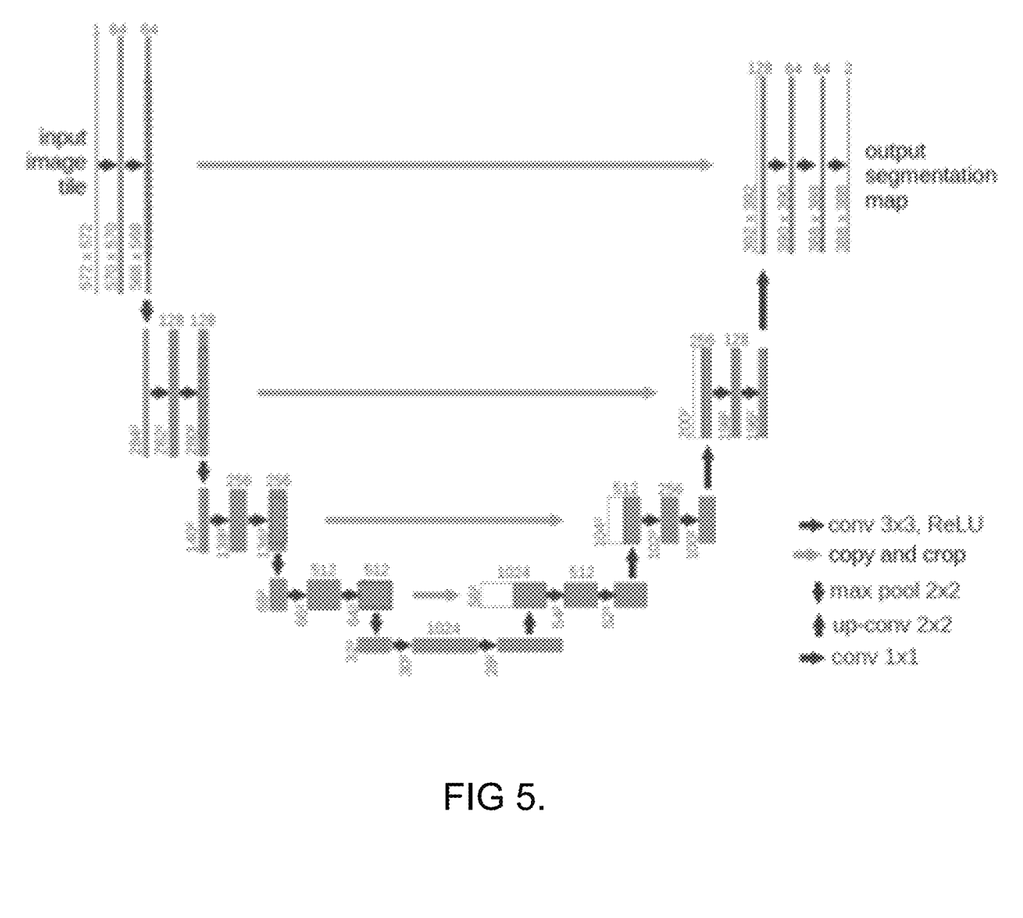
FIG. 5 illustrates an example method for the second stage of the two stage deep neural network.

In the second stage model, referring to FIG. 3 at 303, and FIG. 5, a system may utilize an encoder-decoder network to segment each of the plurality of image slices that are included in each of the plurality of classification groups that were produced in the first stage of the model. In an embodiment, the encoder-decoder network implemented may include a contracting and expanding path. The contracting and expanding paths may each consist of three or more convolutional blocks, where each convolutional block may contain two convolutional layers for filtering, and a ReLU and batch normalization layer for neuron activation. As the image slices are processed by the encoder-decoder network, a system may utilize the outputted segmentation data to produce a probability mask predicting an appendix location.

In an embodiment, the contracting path present in the encoder-decoder network may utilize a max-pooling layer after each convolutional layer to assist in summarizing the segmentations of each image slice passed through. Each slice included in a classification group produced in the first stage model may be analyzed to recognize the appendix specific features. During the training stage, the segmentation may be trained with the cropped DICOM images (CT images) in conjunction with the image slices, to correlate the appendix specific features with possible locations of the appendix. Thus, during a deployment stage, when new image slices are fed through the encoder-decoder network, a system may be able to recognize appendix specific features and make high-quality predictions associated with the possible position of the appendix. All predictions of possible positions for the appendix may be summarized by the max-pooling layer and created into feature maps. The trained contracting path may segment the feature maps until only the highest-quality predictions remain, which are then fed into the expanding path.

In an embodiment, the expanding path in the encoder-decoder network may utilize a transpose layer to upsample the feature maps produced by the contracting path. The feature maps fed into and through the expanding path are those that outlast the segmentation process and have the clearest, highest-quality predictions regarding the position of the appendix. When upsampling the remaining feature maps over a transpose layer, a system may expand the condensed, high-quality feature map predictions produced in the contracting path to assist in providing a possible appendix position. Upsampling may permit a system to act as if it were performing at a higher rate. Thus, when upsampling the produced feature maps, accurate approximations are made regarding the position of the appendix at a greater scale.

In an embodiment, as an attempt to prevent loss of information within the feature maps, the contracting path may be concatenated with the corresponding upsampled feature maps. Concatenating the contracting path with the corresponding upsampled feature maps may increase segmentation accuracy. In an embodiment, after upsampling the feature maps and concatenating the upsampled features maps, a single feature map may be all that remains. This single feature map may then be condensed using a final convolutional layer to produce the feature map as a one channel layer. The one channel layer is influenced by an activation function using a sigmoid function to produce a probability mask relating to where a system believes an appendix is located. Thus, the segmentation layer may include generating a probability mask for each of the probable locations of the appendix in a particular image.

Referring to FIG. 5, an example encoder-decoder network is displayed. An example encoder-decoder network is a U-Net architecture. While a U-Net architecture is described herein, other similar encoder-decoder networks may be utilized. An embodiment may utilize a U-Net architecture to perform the second stage, the segmentation portion, of the process. U-Net is commonly used for image segmentation and works well with small datasets. Further, in an embodiment, the U-Net may be adapted to be used for localization. As can be seen in FIG. 5, the U-Net contains a contracting path (left side) and an expanding path (right side), with each half of the path including three convolutional blocks. Each block is made up of two 3×3 convolutional layers, each followed by a ReLU layer and a batch normalization layer. As mentioned previously and implemented herein, the contracting path is followed by a 2×2 max-pooling layer, and, in the expanding path, a 2×2 transpose layer to upsample the feature maps. The two paths are then connected by a single convolutional block.

In an embodiment, with reference to FIG. 3 at 304, a system may then threshold the probability masks produced from the second stage model to create a binary mask. A binary mask is utilized to easily identify an appendix location in the images that remain. In an embodiment, a system may perform a connected-component analysis to remove outlier "blobs" of high probabilities. Outlier blobs may include those pixels or image locations that appear to include appendix feature information, but likely do not actually include appendix features. For example, if the outlier blobs are located a distance away from the vast majority of appendix specific feature information, the likelihood the appendix is located at that position is low. Thus, these locations are identified as outliers and removed as a probable location. In performing the connected-component analysis, a system may first perform one or more erosion steps with the radius of 1 pixel. These erosion steps may further reduce noise in the image. An embodiment may then select the largest connected-component, and subsequently dilate the region. This dilation may further provide clarity for the image. The dilation may occur more than once to provide better clarity. The final prediction of the position of the appendix may then be identified by the smallest shape, for example, a bounding box, that fits the dilated mask. In other words, after removing the outlier blobs and performing the erosion and dilation steps, the system may produce a bounding shape around the location within the image that includes the final prediction of the location of the appendix.

In the training phase the final bounding shape may be compared with the known location of the appendix. Based upon this comparison the neural network or machine-learning model may further learn information regarding how to predict the location of the appendix. For example, if the bounding shape does not match the known location, the system may refine how appendix features are identified to more accurately predict the location of the appendix. On the other hand, if the bounding shape does match the known location, the system can use this information to confirm the methods used to come to that accurate prediction.

In a deployment stage, the final bounding box may be provided to a health professional as the predicted location of the appendix. Provision (e.g., display on a display screen, etc.) of the bounding shape surrounding the predicted position of the appendix may provide a professional with the location of the appendix in far less time as compared to conventional methods. Thus, using the described system allows a professional to provide information back to a patient in a quicker manner and make a determination of whether surgery is required more quickly than the conventional manual methods. The use of the two stage model described herein drastically negates the influence of human error on a system, which may lead to more consistent accurate localizing of the appendix. By providing a bounding shape around the predicted position of the appendix on a CT image, surgical complications related to acute appendicitis may decrease, and patient survival statistics related to appendicitis may increase. The various embodiments described herein thus represent a technical improvement to determining the location of an appendix within a human.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for training a machine-learning model to detect a location of a person's appendix, comprising:
  receiving, at the machine-learning model, a plurality of images, each image being a slice of a body taken by a CT scan;
  identifying, for each of the plurality of images, features of the appendix, wherein the identifying comprises analyzing a plurality of slices of each of the plurality of images and classifying each of the plurality of slices, into one of a plurality of classification groups, based upon a feature of the appendix within the slice;

segmenting each of the plurality of image slices included in the one of the plurality of classification groups that classifies the slice as containing the appendix, thereby identifying probable locations of the appendix, via utilizing a probability mask for each of the probable locations;

producing a binary mask, from the probability masks, encompassing at least a portion of the probable locations; and producing a smallest bounding shape within the binary mask identifying a final prediction of the location of the appendix.

2. The method of claim 1, further comprising cropping the images, wherein the cropping reduces a size of the image by removing at least a portion of pixels of the image not containing the appendix.

3. The method of claim 1, wherein the producing a binary mask comprises removing outlier probable locations via performing an erosion step and a dilation step.

4. The method of claim 1, wherein identifying features within each of the plurality of slices comprises utilizing cascaded layers of convolutional layers.

5. The method of claim 4, wherein the identifying features comprises performing, between each of the cascaded convolutional layers, max-pooling of operations that summarize feature responses.

6. The method of claim 5, wherein the classifying comprises feeding the feature responses into at least one neural layer, the at least one neural layer making appendix-specific classifications utilizing the feature responses.

7. The method of claim 1, wherein the segmenting comprises utilizing an encoder-decoder network.

8. The method of claim 1, wherein the segmenting comprises utilizing an encoder-decoder network comprising a contracting path and an expanding path, each of the contracting path and the expanding path comprising three or more convolutional blocks, wherein each convolution block comprises two convolutional layers, a rectified linear units layer, and a batch normalization layer;
the contracting path further comprising a max-pooling layer; and
the expanding path further comprising a transpose layer that upsamples a feature map generated from the features of the plurality of slices.

9. The method of claim 8, wherein feature maps are concatenated with corresponding upsampled feature maps.

10. The method of claim 1, wherein the each image being a slice of the body taken by a CT scan comprises a known location of the appendix within the image.

11. An information handling device for training a machine-learning model to detect a location of a person's appendix, comprising:
a processor;
a memory device that stores instructions executable by the processor to:
receive, at the machine learning model, a plurality of images, each image being a slice of a body taken by a CT scan;
identify, for each of the plurality of images, features of the appendix, wherein to identify comprises analyzing a plurality of slices of each of the plurality of images and classifying each of the plurality of slices based upon a feature of the appendix within the slice;
segment each of the plurality of image slices included in slices with the high likelihood of containing the appendix, thereby identifying probable locations of the appendix, via utilizing a probability mask for each of the probable locations;
produce a binary mask, from the probability masks, encompassing at least a portion of the probable locations; and
produce a smallest bounding shape within the binary mask identifying a final prediction of the location of the appendix.

12. The information handling device of claim 11, further comprising cropping the images, wherein the cropping reduces a size of the image by removing at least a portion of pixels of the image not containing the appendix.

13. The information handling device of claim 11, wherein to produce a binary mask comprises removing outlier probable locations via performing an erosion step and a dilation step.

14. The information handling device of claim 11, wherein to identify features within each of the plurality of slices comprises utilizing cascaded layers of convolutional layers.

15. The information handling device of claim 14, wherein to identify features comprises performing, between each of the cascaded of convolutional layers, max-pooling of operations that summarize feature responses.

16. The information handling device of claim 15, wherein the classifying comprises feeding the feature responses into at least one neural layer, the at least one neural layer making appendix-specific classifications utilizing the feature responses.

17. The information handling device of claim 11, wherein the segmenting comprises utilizing an encoder-decoder network.

18. The information handling device of claim 11, wherein to segment comprises utilizing an encoder-decoder network comprising a contracting path and an expanding path, each of the contracting path and the expanding path comprising three or more convolutional blocks, wherein each convolution block comprises two convolutional layers, a rectified linear units layer, and a batch normalization layer;
the contracting path further comprising a max-pooling layer; and
the expanding path further comprising a transpose layer that upsamples a feature map generated from the features of the plurality of slices.

19. The information handling device of claim 18, wherein feature maps are concatenated with corresponding upsampled feature maps.

20. A product for training a machine-learning model to detect a location of a person's appendix, comprising:
a storage device having code stored within, the code being executable by a processor and comprising:
code that receives, at the machine-learning model, a plurality of images, each image being a slice of a body taken by a CT scan;
code that identifies, for each of the plurality of images, features of the appendix, wherein the identifying comprises analyzing a plurality of slices of each of the plurality of images and classifying each of the plurality of slices based upon a feature of the appendix within the slice;
code that segments each of the plurality of image slices included in the one of the plurality of classification groups that classifies the slice as containing the appendix, thereby identifying probable locations of the appendix, via utilizing a probability mask for each of the probable locations;

code that produces a binary mask, from the probability masks, encompassing at least a portion of the probable locations; and code that produces a smallest bounding shape within the binary mask identifying a final prediction of the location of the appendix.

\* \* \* \* \*